United States Patent [19]

Bilbo et al.

[11] Patent Number: 5,776,119
[45] Date of Patent: Jul. 7, 1998

[54] PORTABLE SUCTION UNIT

[76] Inventors: Sharon C. Bilbo, 304 Oakview Dr., Houma, La. 70364; Melanie Watts Barker, 311 Lark Dr., Lockport, La. 70374; Traci R. Bland, 311 Lark Dr., Houma, La. 70360

[21] Appl. No.: 722,994

[22] Filed: Sep. 30, 1996

[51] Int. Cl.[6] .................................................. A61M 1/00
[52] U.S. Cl. ..................... 604/317; 604/319; 604/322; 604/326
[58] Field of Search ................................. 604/317, 318, 604/319, 322, 326, 346, 320, 76, 67

[56] References Cited

U.S. PATENT DOCUMENTS

| | | | |
|---|---|---|---|
| 4,306,558 | 12/1981 | Kurtz et al. | 604/320 |
| 4,710,165 | 12/1987 | McNeil et al. | 604/67 |
| 4,930,997 | 6/1990 | Bennett | 604/319 |
| 4,964,851 | 10/1990 | Larsson | 604/346 |
| 4,994,022 | 2/1991 | Steffler et al. | 604/317 |
| 5,449,347 | 9/1995 | Preen et al. | 604/317 |

*Primary Examiner*—John G. Weiss
*Assistant Examiner*—David J. Cho
*Attorney, Agent, or Firm*—Patent & Trademark Services; Joseph H. McGlynn

[57] ABSTRACT

A portable suction device with a base which includes a pump with a pump outlet and inlet and a battery holder with rechargeable batteries connected to the pump via a switch. The base includes a battery charging jack therein for recharging the batteries from a suitable electric power supply. The suction device includes a collection container with a view window for viewing the contents therein. Within the collection container is a disposable plastic liner which includes a connector for releasably engaging the pump outlet. Integrally formed on the collection container are threads for a screw-on lid and a tubing support for a piece of tubing. The collection container may include a holder for a supply of sterile disposable tubing pieces.

10 Claims, 1 Drawing Sheet

U.S. Patent  Jul. 7, 1998  5,776,119
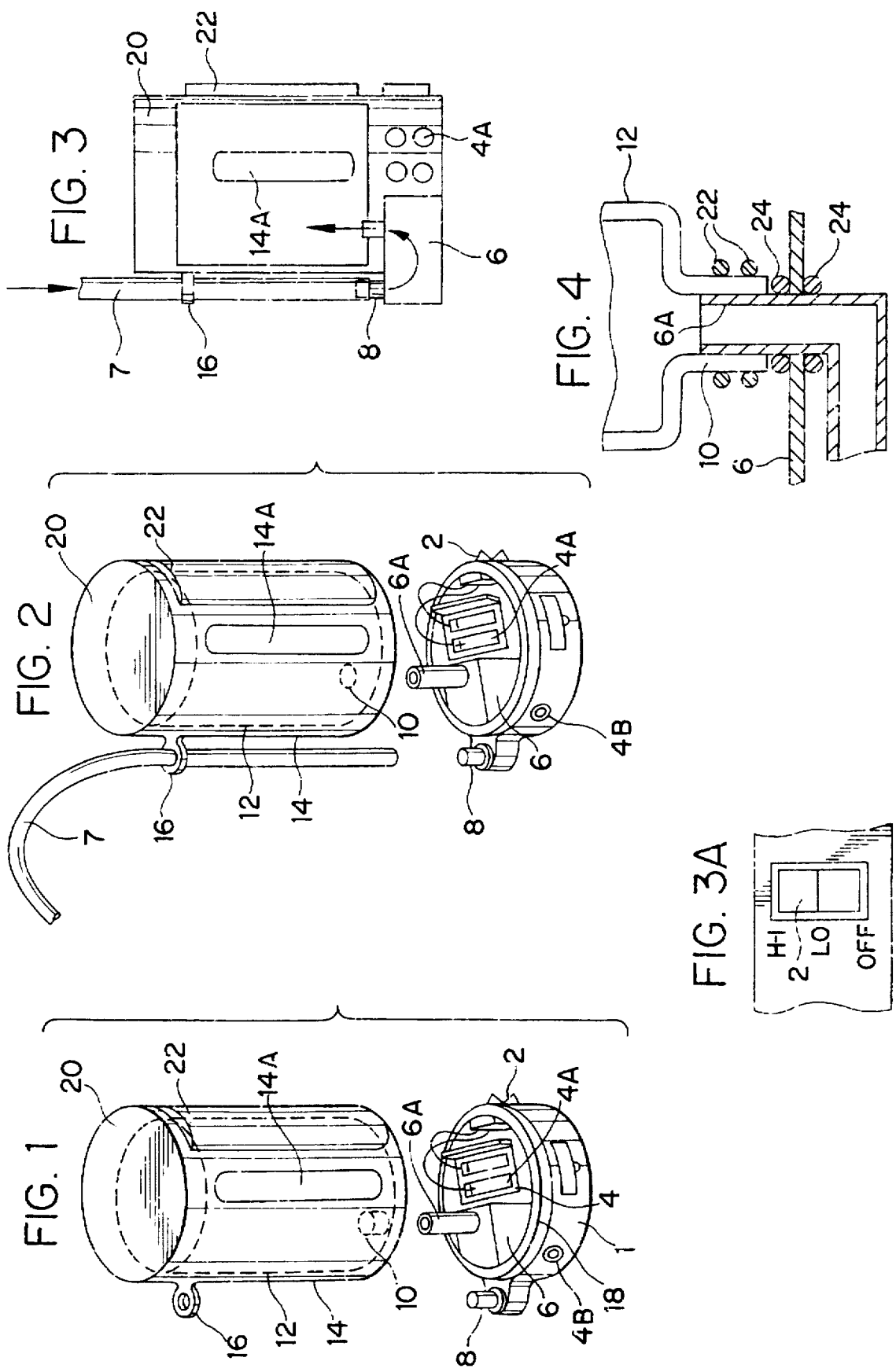

PORTABLE SUCTION UNIT

BACKGROUND OF THE INVENTION

This invention relates, in general, to a portable suction device and in particular, to a portable suction device having batteries and disposable liners and tubes. The batteries may be recharged by a recharger unit.

Description of the Prior Art

Existing suction devices come in a variety of forms ranging from hand powered bellows type suction devices to miniature battery powered versions. A number of devices have been invented in an attempt to perfect portable, suction units. For example, U.S. Pat. No. 5,342,329 discloses a portable, closed circuit, disposable device for post operatory surgical suction which comprises a bellows-shaped body receptacle for suctioned fluids, a threaded neck located on the upper surface of the bellows-shaped body suitable to receive a threaded cap; the cap being provided with a suction tube system connected through the cap into the bellows-shaped body, and the system of tubes is provided with a check-valve. However this device requires manual pumping in order to operate. U.S. Pat. No. 5,318,548 discloses an extractor which is particularly useful for extracting mucus from the nasal passages of new born babies and comprises a manually operable hand pump with a separate compartment for the mucus extracted. This device also has the disadvantage that it must be manually pumped in order to operate.

U.S. Pat. No. 4,969,229 discloses a battery-operated surface treatment apparatus having a booster function. The device which is preferably a vacuum cleaner, comprises an electric motor which drives a suction fan and a battery-powered power supply unit for the motor. Additionally, the apparatus is provided with a coupling device for the activation of the booster function by temporarily connecting a separate battery in series with the batteries in the power supply unit.

U.S. Pat. No. 4,956,892 discloses a cordless vacuum brush which includes a forward vacuum assembly containing a motor, fan, a dust trap and a rearward elongated hollow handle assembly containing a plurality of battery cells connected in series for operating the motor and a built-in battery charger. The rear or free end of the handle assembly is equipped with an end cap having a fold-out connector or plug for plugging into a 120 volt AC outlet.

The prior art devices are either difficult and tiring to use in the case of the manually powered suction devices or complex and requiring many costly parts in the case of the battery powered devices. Thus, there is a need for a portable, battery powered suction device which is simple to manufacture and use and which is economical as well.

SUMMARY OF THE INVENTION

The present invention is directed to a portable battery powered suction device which uses a vacuum suction unit 6 mounted along the bottom of a circular casing made of molded plastic. One section of the casing has a clear view window 14a and another section has a holder for disposable suction tubes 22. These tubes are placed along the side of the unit through the tube holder and onto the tubing connector at the pump input 8. Inside the main body of the portable suction device is a sterile, disposable liner made from polyethylene plastic 12. The disposable liner is connected to the output of the pump by way of a connector 10, which slides over the output of the pump 6a, which is located inside the collection jar 14. Below the tubing dispenser is a three position switch 2, which allows a user to use the portable suction device at high power, low power, or to switch the device off. At the bottom of the device is a compartment for a series of rechargeable batteries 4a and a socket for a recharger unit, so that the user could recharge the batteries from within the unit.

The present invention is significantly different from the prior art devices in that it is easy to manufacture and use, does not fatigue the user and is economical.

It is an object of the present invention to provide a portable suction device which is simply constructed and easy to use.

It is another object of the present invention to provide a portable suction device which is economical for the manufacturer to make and for the user to buy.

These and other objects and advantages of the present invention will be fully apparent from the following description, when taken in connection with the annexed drawings.

BRIEF DESCRIPTION OF THE DRAWINGS

FIG. 1 is an exploded perspective view of the present invention.

FIG. 2 is an exploded perspective view of the present invention with a disposable tubing.

FIG. 3 is a cutaway view of the present invention showing flow through the tubing and pump and into the plastic liner.

FIG. 3A is a partial detailed view of the three position switch of the present invention.

FIG. 4 is a detailed view of the connection between pump outlet and the plastic liner connector.

DESCRIPTION OF THE PREFERRED EMBODIMENT

Referring now to the drawings in greater detail, FIG. 1 shows an exploded view of the portable suction device of the present invention with a base 1. The base includes a pump 6 with a pump outlet 6A and inlet 8 and a battery compartment 4 with rechargeable batteries 4A connected to the pump via a switch 2. The base includes a battery charging jack 4B therein for recharging the batteries from a suitable electric power supply.

The suction device includes a collection container 14 with a view window 14A therein. Within the collection container is a disposable plastic liner 12 (shown in dotted lines in FIG. 1) which includes a depending sleeve 10 for releasably engaging the pump outlet 6A (see FIG. 4). Integrally formed on the collection container are threads 18 for connecting the base 1 to the container 14. The container has a top 20 and a tubing support 16 for a piece of tubing 7 (shown in FIG. 2). The collection container may also include a holder 22 on the side of the container 14 for holding a supply of sterile disposable tubing pieces 7.

FIG. 4 shows a detailed view of the sleeve 10 of plastic liner 12 engaged on the outlet 6A of pump 6. O-rings 22 are placed around the sleeve 10 to seal the connector to the outside surface of outlet 6A. In addition, O-rings 24 seal the opening where the tube penetrates into the pump unit 6.

FIG. 3 shows a view of the portable suction device of the present invention with a piece of disposable plastic tubing 7 extending through the tubing support 16 of the collection container and connected to the inlet 8 of the pump. The arrows in FIG. 3 indicate flow through the plastic tubing and pump and into the disposable plastic liner when the pump is energized.

FIG. 3A shows a detail view of the three position function switch which may be placed in either the "off", "high", or "low" speed positions. Obviously, these positions are shown merely for illustration purposes, and more or fewer positions for the switch could be included without departing from the scope of the invention.

In use, a user would select a length of suction tubing 7 from the front mounted tubing supply holder or dispenser 22, then place the tubing along the side of the unit, engaging the tubing onto the pump inlet 8. Next, the user would turn the portable suction device to the high or low position, and begin to draw mucus, sputum or other bodily fluids into the disposable liner 12 inside the main body of the unit. When the user is finished, he/she would switch the control to the off position, unscrew the base 1 and then dispose of the suction tubing and the plastic liner. When the liner is to be replaced, the user unscrews the base 1, then replaces the liner 12, making sure that the O-rings 22, 24 are positioned properly, and replaces the base 1 for later use.

In the event that the battery power becomes low, a user may place the plug of a conventional battery recharger unit (not shown) into the recharger socket 4B, then place the other end of the recharger unit into a wall mounted electrical outlet and allows the depleted batteries to charge.

Use of the portable suction device would aid in the removal of mucus or sputum from newborns and infants, allergy sufferers, and would aid in keeping tracheotomy patients clear and breathing normally. The portable suction device is cleaned and sterilized by using a clean suction tube and sucking alcohol or hydrogen peroxide through the device, using the built in pump, thereby cleaning the pump and all other components.

The primary components of the portable suction device would be best manufactured using the plastic injection molding process. Injection molding is a plastic molding procedure whereby heat softened plastic material is forced under very high pressure into a metal cavity mold which is relatively cool. Acceptable metals for the mold are aluminum and steel. The inside cavity of the mold is comprised of two or more halves, and is the same desired shape as the product to be formed. High pressure hydraulics are used to keep the mold components together during the actual injection phase of the molding process. The injected plastic is allowed to cool and harden. The hydraulics holding the multiple component cavity together are released, the halves of the mold separated and the solid formed plastic item is removed. Injection molding can be a highly automated process and is capable of producing extremely detailed parts at a cost effective price. This process should be invaluable for producing the portable suction device cost effectively. The pump unit is available as an off the shelf unit. The plastic liner may also be available as a modified off the shelf item.

Although the portable suction device and the methods of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A portable suction device for use in removing mucus, sputum and other body fluids comprising:

a base including a pump with an inlet and an outlet opening, a source of electrical power operatively connected to said pump with a switch for controlling said pump, tubing detachably connected at one end to said pump inlet, a collection container having an open bottom attached to said base, a liner within said collection container, means connected to said liner for sealing said liner to said pump outlet, and means for closing said open bottom of said collection container, and wherein said means for closing said open bottom has an inlet tube with a first and second end connected to said pump at one of said ends, another end of said inlet tube projecting into said collection chamber when said means for closing said open bottom is connected to collection chamber, said liner being sealingly connected to another end of said inlet tube.

2. The portable suction device as claimed in claim 1, wherein said electrical power source is at least one battery.

3. The portable suction device as claimed in claim 1, wherein said electrical power source includes at least one rechargeable battery and a battery charging jack is operatively connected to said at least one battery.

4. The portable suction device as claimed in claim 1, wherein said electric switch is a three position switch with high power, low power and off positions.

5. The portable suction device as claimed in claim 1, wherein said collection container includes a view window for viewing contents of the container.

6. The portable suction device as claimed in claim 1, wherein said collection container includes means adjacent said top of said container for supporting said tubing, and means for holding extra tubing pieces.

7. The portable suction device as claimed in claim 1, wherein said means connected to said liner for sealing said liner to said pump outlet is at least one O-ring.

8. The portable suction device as claimed in claim 1, wherein said means for closing said open bottom completely closes said open bottom in order to protect said liner.

9. The portable suction device as claimed in claim 1, wherein said means for closing said open bottom has a top and bottom portion, and said means for closing said open bottom has said source of electrical power attached thereto.

10. The portable suction device as claimed in claim 1, wherein said liner has an aperture, another end of said inlet tube projecting into said aperture, means surrounding said aperture for sealing said aperture to said another end of said inlet tube.

* * * * *